US00PP19216P2

(12) United States Plant Patent
Dümmen

(10) Patent No.: US PP19,216 P2
(45) Date of Patent: Sep. 16, 2008

(54) ***PETUNIA* PLANT NAMED 'DUESURPRILA'**

(50) Latin Name: *Petunia×hybrida*
Varietal Denomination: Duesurprila

(75) Inventor: Tobias Dümmen, Rheinberg (DE)

(73) Assignee: Capitol Green Investments Ltd.., Grand Cayman (KY)

( * ) Notice: Subject to any disclaimer, the term of this patent is extended or adjusted under 35 U.S.C. 154(b) by 0 days.

(21) Appl. No.: 11/804,350

(22) Filed: May 17, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent L. Bell
*Assistant Examiner*—Annette H Para
(74) *Attorney, Agent, or Firm*—C. A. Whealy

(57) ABSTRACT

A new and distinct cultivar of *Petunia* plant named 'Duesurprila', characterized by its outwardly spreading to trailing growth habit; freely branching habit; early and freely flowering habit; large light purple-colored flowers; and good garden performance.

1 Drawing Sheet

Botanical designation: *Petunia×hybrida.*
Cultivar denomination: 'DUESURPRILA'.

BACKGROUND OF THE INVENTION

The present invention relates to a new and distinct cultivar of *Petunia,* botanically known as *Petunia×hybrida* and hereinafter referred to by the name 'Duesurprila'.

The new *Petunia* is a product of a planned breeding program conducted by the Inventor in Rheinberg, Germany. The objective of the breeding program is to create new *Petunia* cultivars with early and freely flowering habit, and unique and attractive flower color.

The new *Petunia* originated from a cross-pollination made by the Inventor in August, 2004 in Rheinberg, Germany of a proprietary selection of *Petunia×hybrida* identified as code number E-19-23, not patented, as the female, or seed, parent with a proprietary selection of *Petunia×hybrida* identified as code number 01-0016-07, not patented, as the male, or pollen, parent. The new *Petunia* was discovered and selected by the Inventor as a single flowering plant within the progeny of the stated cross-pollination in a controlled environment in Rheinberg, Germany in May, 2005.

Asexual reproduction of the new *Petunia* by terminal cuttings in a controlled environment in Rheinberg, Germany since July, 2005, has shown that the unique features of this new *Petunia* are stable and reproduced true to type in successive generations.

SUMMARY OF THE INVENTION

The cultivar Duesurprila has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duesurpila'. These characteristics in combination distinguish 'Duesurprila' as a new and distinct cultivar of *Petunia:*

1. Outwardly spreading to trailing growth habit.
2. Freely branching habit.
3. Early and freely flowering habit.
4. Large light purple-colored flowers.
5. Good garden performance.

Plants of the new *Petunia* can be compared to plants of the female parent selection. Plants of the new *Petunia* differ from plants of the female parent selection in the following characteristics:

1. Plants of the new *Petunia* are more vigorous than plants of the female parent selection.
2. Plants of the new *Petunia* and the female parent selection differ in flower color as plants of the female parent selection have white-colored flowers.

Plants of the new *Petunia* can be compared to plants of the male parent selection. Plants of the new *Petunia* differ from plants of the male parent selection in the following characteristics:

1. Plants of the new *Petunia* are more vigorous than plants of the male parent selection.
2. Plants of the new *Petunia* and the male parent selection differ in flower color as plants of the male parent selection have pink-colored flowers.

Plants of the new *Petunia* can be compared to plants of the *Petunia* cultivar Duesurlav, disclosed in U.S. Plant Pat. No. 13,553. In side-by-side comparisons conducted in Rheinberg, Germany, plants of the new *Petunia* differed from plants of the cultivar Duersurlav in the following characteristics:

1. Plants of the new *Petunia* were larger and more vigorous than plants of the cultivar Duesurlav.
2. Plants of the new *Petunia* had longer internodes than plants of the cultivar Duesurlav.
3. Plants of the new *Petunia* had larger leaves and shorter petioles than plants of the cultivar Duesurlav.
4. Plants of the new *Petunia* had larger flowers than plants of the cultivar Duesurlav.
5. Plants of the new *Petunia* had shorter peduncles than plants of the cultivar Duesurlav.

BRIEF DESCRIPTION OF THE PHOTOGRAPH

The accompanying colored photograph illustrates the overall appearance of the new *Petunia,* showing the colors as true as it is reasonably possible to obtain in colored reproductions of this type. Colors in the photograph may differ slightly from the color values cited in the detailed botanical description which accurately describe the colors of the new *Petunia.* The photograph comprises a close-up view of typical leaves and flowers of 'Duesurprila'.

DETAILED BOTANICAL DESCRIPTION

The photograph and following observations, measurements and values describe plants grown in Rheinberg, Germany, under commercial practice during the spring in a glass-covered greenhouse with day and night temperatures averaging 18° C. and light levels averaging 4,500 lux. Rooted young plants had been growing for about 16 weeks when the photograph and description were taken. Plants were pinched one time about three weeks after planting. In the following description, color references are made to The Royal Horticultural Society Colour Chart, 2001 Edition, except where general terms of ordinary dictionary significance are used.

Botanical classification: *Petunia×hybrida* cultivar Duesurprila.

Parentage:

*Female, or seed, parent.*—Proprietary selection of *Petunia×hybrida* identified as code number E-19-23, not patented.

*Male, or pollen, parent.*—Proprietary selection of *Petunia×hybrida* identified as code number 01-0016-07, not patented.

Propagation:

*Type.*—by terminal cuttings.

*Time to initiate roots, summer.*—About seven days at temperatures of 20° C.

*Time to initiate roots, winter.*—About ten days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching; dense.

Plant description:

*Plant and growth habit.*—Outwardly spreading to trailing growth habit. Freely branching habit with about eight to ten lateral branches developing from the pinch. Moderately vigorous growth habit.

*Plant height.*—About 28 cm.

*Plant diameter.*—About 35 cm.

Lateral branch description:

*Length.*—About 30 cm.

*Diameter.*—About 4 mm.

*Internode length.*—About 3.3 cm.

*Strength.*—Moderately strong.

*Aspect.*—Initially upright to outwardly spreading.

*Texture.*—Pubescent.

*Color.*—144A to 144B.

Foliage description:

*Arrangement.*—Before flowering, alternate, simple; after flowering, opposite, simple.

*Length.*—About 5.7 cm.

*Width.*—About 3.3 cm.

*Shape.*—Spatulate to ovate.

*Apex.*—Acute.

*Base.*—Attenuate.

*Margin.*—Entire.

*Texture, upper and lower surfaces.*—Pubescent.

*Venation pattern.*—Pinnate; arcuate.

*Color.*—Developing and fully expanded foliage, upper surface: 137A; venation, 144B. Developing and fully expanded foliage, lower surface: 137C; venation, 144b.

*Petiole length.*—About 5.6 mm.

*Petiole diameter.*—About 2.6 mm.

*Petiole texture, upper and lower surfaces.*—Pubescent.

*Petiole color, upper and lower surfaces.*—144B.

Flower description:

*Flower arrangement and habit.*—Relatively large salverform flowers; singly arising from leaf axils. Freely flowering habit with usually about 25 to 30 open flowers and flower buds per plant. Flowers persistent. Flowers face upright to outwardly.

*Fragrance.*—None detected.

*Natural flowering season.*—Plants flower continuously from late spring into autumn in Germany. Early flowering habit, plants typically beginning flowering about nine weeks after planting.

*Flower longevity.*—Individual flowers last about five days on the plant.

*Flower diameter.*—About 6.5 cm.

*Flower length (height).*—About 2.9 cm.

*Flower throat diameter.*—About 1.2 cm.

*Flower tube diameter.*—About 3 mm.

*Flower bud.*—Shape: Ovoid. Length: About 4.9 cm. Diameter: About 8 mm. Color: 144B tinted with 79B.

*Corolla.*—Arrangement: Five petals fused at the base and opening into a flared trumpet. Petal length from throat: About 3.4 cm. Petal lobe width: About 3.2 cm. Petal shape: Spatulate. Petal apex: Acute. Petal margin: Entire. Petal texture, upper and lower surfaces: Smooth, glabrous; satiny. Throat texture: Smooth, glabrous. Tube texture: Pubescent. Color: Petal, when opening and fully opened, upper surface: 78B; venation, 79B. Petal, when opening and fully opened, lower surface: 82B; venation, 152A. Flower throat: 79A and 144B; venation, 79A to 79B. Flower tube: 79A to 79B; venation, 152A.

*Calyx.*—Arrangement: One star-shaped calyx tube with five sepals fused at the base per flower. Sepal length: About 3 cm. Sepal width: About 5 mm. Sepal shape: Narrowly oblong. Sepal apex: Rounded. Sepal margin: Entire. Sepal texture, upper and lower surfaces: Pubescent. Color, immature and mature, upper surface: 137A. Color, immature and mature, lower surface: 137C.

*Peduncles.*—Length: About 3.3 cm. Diameter: About 2 mm. Strength: Moderately strong. Texture: Pubescent. Color: 144B.

*Reproductive organs.*—Stamens: Quantity/arrangement: Five per flower. Anther shape: Ovate. Anther length: About 2.5 mm. Anther color: 91A. Pollen amount: Abundant. Pollen color: 122B. Pistils: Quantity: One per flower. Pistil length: About 2.3 cm. Style color: 145C. Stigma shape: Rounded. Stigma color: 103A. Ovary color: 144B. Seed/fruit: Seed and fruit development have not been observed on plants of the new *Petunia.*

Garden performance: Plants of the new *Petunia* have been observed to have good garden performance and tolerate wind, rain and temperatures ranging from about 2° C. to about 38° C.

Pathogen/pest resistance: Plants of the new *Petunia* have not been observed to be resistant to pathogens and pests common to *Petunia.*

It is claimed:

1. A new and distinct *Petunia* plant named 'Duesurprila' as illustrated and described.

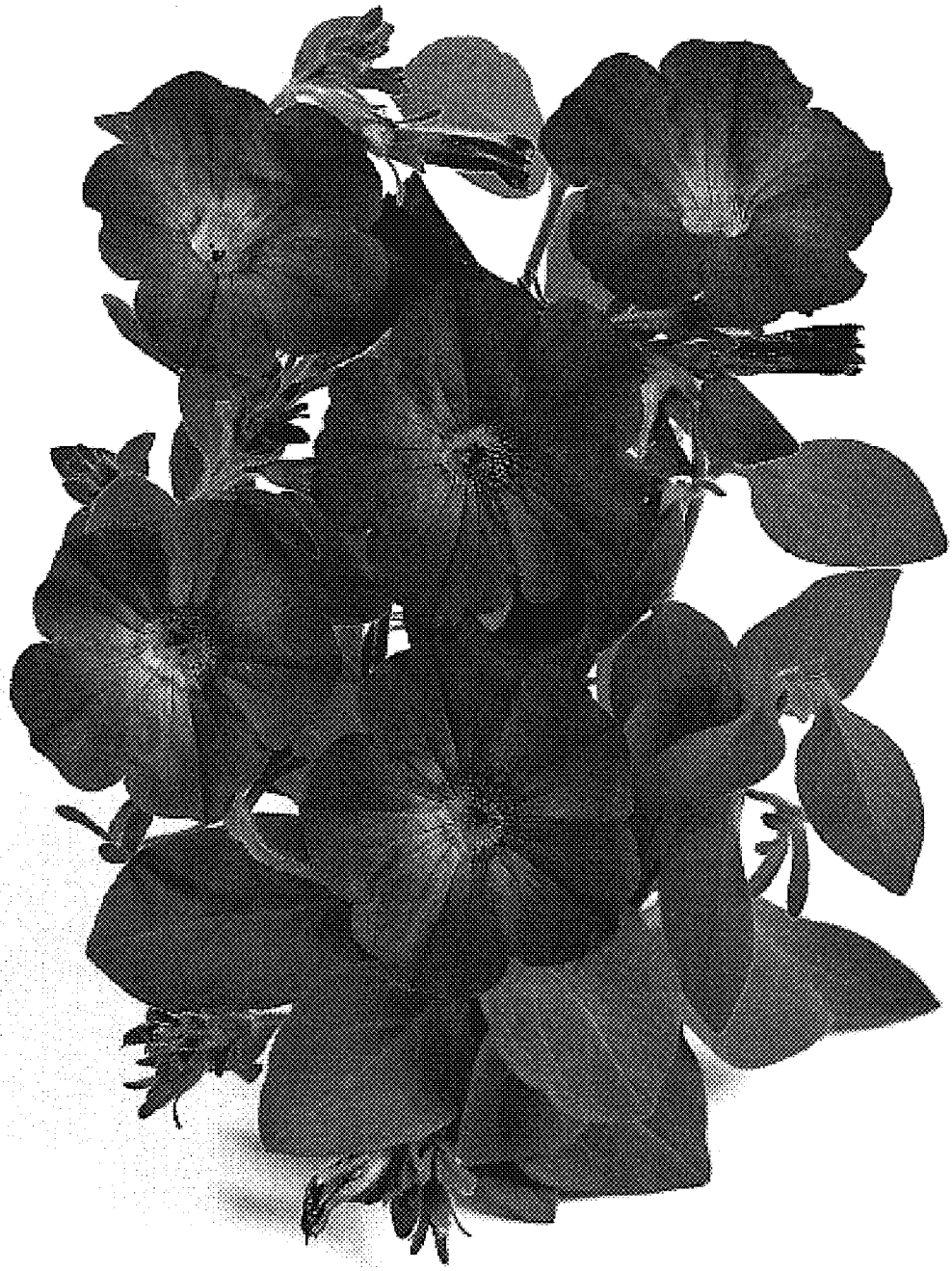

* * * * *